United States Patent
Wu et al.

(10) Patent No.: US 11,174,476 B2
(45) Date of Patent: Nov. 16, 2021

(54) ORGANIC-INORGANIC HYBRID NANOFLOWER AND PREPARATION METHOD THEREOF

(71) Applicant: Guilin University of Technology, Guilin (CN)

(72) Inventors: Xiaoli Wu, Guilin (CN); Ke Ren, Guilin (CN); Mengwu Wang, Guilin (CN); Zewen He, Guilin (CN); Shaoling Peng, Guilin (CN); Jichan Ning, Guilin (CN); Yuanli Liu, Guilin (CN)

(73) Assignee: Guilin University of Technology, Guilin (CN)

( * ) Notice: Subject to any disclaimer, the term of this patent is extended or adjusted under 35 U.S.C. 154(b) by 0 days.

(21) Appl. No.: 16/991,660

(22) Filed: Aug. 12, 2020

(65) Prior Publication Data
US 2021/0230574 A1    Jul. 29, 2021

(30) Foreign Application Priority Data

Sep. 10, 2019  (CN) .......................... 201910854715.6

(51) Int. Cl.
| | |
|---|---|
| *C12N 11/14* | (2006.01) |
| *C12N 9/08* | (2006.01) |
| *C01F 17/276* | (2020.01) |
| *C12N 9/02* | (2006.01) |
| *C12N 9/26* | (2006.01) |

(52) U.S. Cl.
CPC ............ *C12N 11/14* (2013.01); *C01F 17/276* (2020.01); *C12N 9/0061* (2013.01); *C12N 9/0065* (2013.01); *C12N 9/2414* (2013.01); *C12Y 110/03002* (2013.01); *C12Y 111/01007* (2013.01); *C12Y 302/01001* (2013.01); *C01P 2002/82* (2013.01); *C01P 2004/03* (2013.01)

(58) Field of Classification Search
None
See application file for complete search history.

(56) References Cited

PUBLICATIONS

Organic-inorganic hybrid nanoflowers: types, characteristics, and future prospects, Nanobiotechnol (2015) 13:54.*

* cited by examiner

*Primary Examiner* — Suzanne M Noakes
*Assistant Examiner* — Jae W Lee
(74) *Attorney, Agent, or Firm* — Jordan IP Law, LLC; Todd A. Vaughn

(57) ABSTRACT

The technical field of enzyme immobilization, and particularly, an organic-inorganic hybrid nanoflower and a preparation method thereof. The organic-inorganic hybrid nanoflower is a flower-like immobilized enzyme formed by self-assembly of a layered rare earth compound as an inorganic carrier and a biological enzyme as an organic component. The layered rare earth compound is $Ln_2(OH)_5NO_3 \cdot nH_2O$, where Ln is one or more of La, Ce, Pr, Nd, Sm, Eu, Gd, Tb, Dy, Ho, Er, Tm, Yb, or Y, and n=1.1-2.5. The biological enzyme is one or more of α-amylase, horseradish peroxidase, or laccase. A layered rare earth compound is used as the inorganic carrier for the organic biological enzyme to form the flower-like immobilized enzyme. The immobilized enzyme has better stability and higher catalytic performance when compared with a free enzyme.

1 Claim, 7 Drawing Sheets

ORGANIC-INORGANIC HYBRID NANOFLOWER AND PREPARATION METHOD THEREOF

CROSS REFERENCE TO RELATED APPLICATIONS

The present application claims priority to Chinese Patent Application No. 201910854715.6 (filed on Sep. 10, 2019), the entire content of which is incorporated herein by reference in its complete entirety.

TECHNICAL FIELD

The present invention relates to the technical field of enzyme immobilization, in particular to an organic-inorganic hybrid nanoflower and a preparation method thereof.

BACKGROUND

Biological enzyme is an important biological catalyst which is highly specific and highly catalytic. However, industrial application of an enzyme still faces challenges due to limitations of the enzyme itself or relative process parameters, for example, poor stability, difficulty in recycle and relatively high production cost.

Enzyme immobilization technology can break these limitations effectively. Compared with a free enzyme, an immobilized enzyme has the advantages of increased stability, improved reusability and easier product separation. However, immobilized biological enzymes have reduced catalytic performance since most immobilized enzymes are synthesized under harsh conditions, for example, high temperature, high pressure or use of toxic organic solvents. This prevents the wide use of these biological catalytic systems. Therefore, how to improve activities of immobilized enzymes has become an urgent problem to be solved.

SUMMARY

In view of this, an objective of the present invention is to provide an organic-inorganic hybrid nanoflower and a preparation method thereof. The present invention uses a layered rare earth compound as an inorganic carrier for a biological enzyme to form a flower-like immobilized enzyme which has excellent stability and higher catalytic performance compared with a corresponding free enzyme. Moreover, the preparation method provided by the present invention adopts mild conditions in a simple process which takes a relatively short time.

In order to realize the objective of the present invention, the present invention provides the following technical solutions.

The present invention provides an organic-inorganic hybrid nanoflower by self-assembly of a layered rare earth compound as an inorganic carrier and a biological enzyme as an organic component to form a flower-like immobilized enzyme, where the layered rare earth compound is $Ln_2(OH)_5NO_3 \cdot nH_2O$, where Ln is one or more of La, Ce, Pr, Nd, Sm, Eu, Gd, Tb, Dy, Ho, Er, Tm, Yb or Y, and n=1.1-2.5; and the biological enzyme is one or more of α-amylase, horseradish peroxidase or laccase.

The present invention further provides a preparation method for the above organic-inorganic hybrid nanoflower, including the following steps:

(1) mixing a rare earth nitrate aqueous solution with a biological enzyme to obtain a mixed solution, where a rare earth ion in a rare earth nitrate is one or more of La, Ce, Pr, Nd, Sm, Eu, Gd, Tb, Dy, Ho, Er, Tm, Yb or Y;

(2) adding ammonium nitrate and ammonia water in sequence to the mixed solution, and then aging to obtain an aged solution;

(3) centrifuging, washing and drying the aged solution in sequence to obtain the organic-inorganic hybrid nanoflower.

Preferably, the rare earth ion in the rare earth nitrate aqueous solution has a molar concentration of 0.005-1 mol/L.

Preferably, the biological enzyme in the rare earth nitrate aqueous solution has a concentration of 0.001-3 mg/mL.

Preferably, the mixing is carried out at 15-60° C.

Preferably, the molar ratio of the ammonium nitrate to the rare earth ion is (1-10):1.

Preferably, the mixed solution after addition of ammonia water has a pH of 5-8.

Preferably, the aging is carried out for 12-72 h.

Preferably, the washing is carried out specifically by using water and absolute ethanol in sequence.

Preferably, the drying is carried out at 30-60° C.

The present invention provides an organic-inorganic hybrid nanoflower by self-assembly of a layered rare earth compound as an inorganic carrier and a biological enzyme as an organic component to form a flower-like immobilized enzyme, where the layered rare earth compound is $Ln_2(OH)_5NO_3 \cdot nH_2O$, where Ln is one or more of La, Ce, Pr, Nd, Sm, Eu, Gd, Tb, Dy, Ho, Er, Tm, Yb or Y, and n=1.1-2.5; and the biological enzyme is one or more of α-amylase, horseradish peroxidase or laccase. For the first time, the present invention uses the layered rare earth compound as the inorganic carrier for the organic biological enzyme. The rare earth ion in the layered rare earth compound offers an unoccupied orbit for coordination with a free enzyme. The special layered structure offers space for adsorption of the enzyme while synergy between the rare earth ion and the biological enzyme improves the catalytic performance of the immobilized enzyme. Moreover, compared with zero-dimensional nanoparticles and one-dimensional nanotubes or nanorods, flower-like morphology gives a higher specific surface area and surface energy. Thus, mass transfer between the immobilized enzyme and its substrate is increased which further improves the catalytic performance of the enzyme. Thus, the flower-like immobilized enzyme of the present invention formed by the layered rare earth compound as the inorganic carrier for the biological enzyme has an excellent stability and higher catalytic performance compared with the free enzyme. And the stability of the immobilized enzyme allows better storage and convenient separation from a product in actual applications.

The present invention provides a preparation method for the organic-inorganic hybrid nanoflower. The present invention prepares the organic-inorganic hybrid nanoflower by a coprecipitation method at a relatively low temperature. The method adopts mild conditions in a simple process which takes a relatively short time and adopts a temperature range within which the enzyme has an activity.

DETAILED DESCRIPTION

Figure 1A:
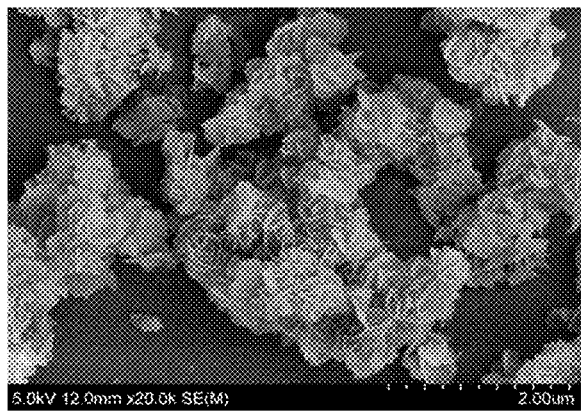
FIGS. 1A and 1B are SEM images of the organic-inorganic hybrid nanoflower prepared in Example 1 with different magnifications for the left (FIG. 1A) and the right (FIG. 1B) images.

The present invention provides an organic-inorganic hybrid nanoflower by self-assembly of a layered rare earth compound as an inorganic carrier and a biological enzyme as an organic component to form a flower-like immobilized enzyme, where the layered rare earth compound is $Ln_2(OH)_5NO_3 \cdot nH_2O$, where Ln is one or more of La, Ce, Pr, Nd, Sm, Eu, Gd, Tb, Dy, Ho, Er, Tm, Yb or Y, and n=1.1-2.5; and the biological enzyme is one or more of α-amylase, horseradish peroxidase or laccase.

For the first time, the present invention uses the layered rare earth compound as the inorganic carrier for the organic biological enzyme. The rare earth ion in the layered rare earth compound offers an unoccupied orbit for coordination with a free enzyme. The special layered structure offers space for adsorption of an enzyme while synergy between the rare earth ion and the biological enzyme improves the catalytic performance of the immobilized enzyme. Moreover, compared with zero-dimensional nanoparticles and one-dimensional nanotubes or nanorods, flower-like morphology gives a higher specific surface area and surface energy. Thus, mass transfer between the immobilized enzyme and its substrate is increased which further improves the catalytic performance of the enzyme. The present invention uses a layered rare earth compound as an inorganic carrier for a biological enzyme to form a flower-like immobilized enzyme which has excellent stability and higher catalytic performance compared with a free enzyme. The stability of the immobilized enzyme allows better storage and convenient separation from a product in actual applications.

The present invention further provides a preparation method for the organic-inorganic hybrid nanoflower in the above solution, including the following steps:

(1) mixing a rare earth nitrate aqueous solution with a biological enzyme to obtain a mixed solution, where a rare earth ion in a rare earth nitrate is one or more of La, Ce, Pr, Nd, Sm, Eu, Gd, Tb, Dy, Ho, Er, Tm, Yb or Y;

(2) adding ammonium nitrate and ammonia water in sequence to the mixed solution, and then aging to obtain an aged solution;

(3) centrifuging, washing and drying the aged solution in sequence to obtain the organic-inorganic hybrid nanoflower.

In the present invention, a rare earth nitrate aqueous solution is mixed with a biological enzyme to obtain a mixed solution. In the present invention, the rare earth nitrate aqueous solution is obtained preferably by dissolving rare earth nitrate into water. In the present invention, the rare earth nitrate is preferably $Ln(NO3)3 \cdot 6H2O$, where Ln is one or more of La, Ce, Pr, Nd, Sm, Eu, Gd, Tb, Dy, Ho, Er, Tm, Yb or Y. In the present invention, the water is preferably deionized water, and the rare earth ion (the Ln ion) in the rare earth nitrate aqueous solution has a molar concentration of preferably 0.005-1 mol/L, and more preferably 0.1-0.5 mol/L. There is no special requirement on a source of the rare earth nitrate in the present invention, and a commercially available product well known in the art can be used.

In the present invention, the biological enzyme in the rare earth nitrate aqueous solution preferably has a concentration of 0.001-3 mg/mL and more preferably 0.5-2.5 mg/mL. In the present invention, the mixing of the rare earth nitrate aqueous solution with the biological enzyme is carried out at preferably 15-60° C., more preferably 20-40 and most preferably 30. The present invention prepares the organic-inorganic hybrid nanoflower at a relatively low temperature which is mild and which keeps the enzyme active. In the present invention, the mixing is carried out preferably by adding the biological enzyme into the rare earth nitrate aqueous solution preferably under stirring. There is no special requirement on speed and time of the stirring in the present invention as long as the biological enzyme and the rare earth nitrate aqueous solution are well mixed. There is no special requirement on a source of the biological enzyme in the present invention, and a commercially available biological enzyme may be used.

After the mixed solution is obtained, ammonium nitrate and ammonia water are added in sequence to the mixed solution, and then aging is carried out to obtain an aged solution. In the present invention, the molar ratio of the ammonium nitrate and the rare earth ion is preferably (1~10):1, more preferably (5-6):1. In the present invention, the ammonium nitrate is preferably added under stirring. There is no special requirement on speed and time of the stirring in the present invention as long as the ammonium nitrate is well mixed in the mixed solution. In the present invention, the ammonium nitrate is added to the mixed solution to provide sufficient nitrate ion for better formation of the layered rare earth compound to immobilize the enzyme. When the amount of ammonium nitrate added is too small, the effect is not obvious since the concentration of nitrate ion is too low. When the amount of ammonium nitrate added is too large, the solution becomes acidic which is harmful to the activity of the biological enzyme. In the present invention, the ammonia water is preferably added dropwise. After addition of the ammonia water, the mixed solution is preferably at a pH of 5-8, and more preferably 6.

In the present invention, the ammonia water is added to adjust the pH of the solution on one hand, and provide sufficient $OH^-$ to form the layered rare earth compound on the other hand. In the present invention, the aging is carried out at preferably 15-60° C., and more preferably 20-40° C. for preferably 12-72 h, and more preferably 20-60 h. In the present invention, the aging is beneficial for formation of the layered rare earth compound and facilitates self-assembly of the biological enzyme with the layered rare earth compound to obtain the organic-inorganic hybrid nanoflower. The present invention prepares the organic-inorganic hybrid nanoflower by a coprecipitation method as follows: mixing a rare earth nitrate solution with a biological enzyme where the biological enzyme is dissolved into the rare earth nitrate solution to obtain a uniform and stable precursor solution; then gradually adding ammonium nitrate and ammonia water to the precursor solution where the biological enzyme is uniformly self-assembled with the layered rare earth compound $Ln_2(OH)_5NO_3 \cdot nH_2O$ coprecipitated by the rare earth nitrate, the ammonium nitrate and the ammonia water, and forms the organic-inorganic hybrid nanoflower.

After the aged solution is obtained, centrifuging, washing and drying of the aged solution are performed in sequence to obtain the organic-inorganic hybrid nanoflower. The present invention has no special requirements on a centrifuging method, and a solid-liquid separation method well known in the art can be used to treat the aged solution. In the present invention, the washing is carried out specifically by using deionized water and absolute ethanol in sequence. The present invention has no special requirements on washing times as long as a solid obtained by centrifugation can get clean. In the present invention, the drying is carried out at preferably 30-60° C., and more preferably 40-50° C. The present invention has no special requirements on time of drying as long as water can be removed from a washed solid.

The present invention provides a preparation method for the above organic-inorganic hybrid nanoflower. The preparation method of the present invention adopts mild conditions in a simple process which takes a relatively short time and adopts a temperature range within which the enzyme has an activity.

The organic-inorganic hybrid nanoflower provided by the present invention and preparation method thereof are described in detail by the following examples, but it should not be considered as limiting the scope of the present invention.

Example 1

(1) $Y(NO_3)_3 \cdot 6H_2O$ was dissolved in deionized water to prepare a yttrium nitrate solution with an overall concentration of rare earth ion of 0.5 mol/L;

(2) a certain amount of yttrium nitrate solution prepared by step (1) was added with horseradish peroxidase in a concentration of 2.5 mg/mL based on the yttrium nitrate solution at 15° C., and stirred well;

(3) a mixed solution obtained by step (2) was added with ammonium nitrate in a concentration of 1.5 mol/L based on the mixed solution and stirred well;

(4) a mixed solution obtained by step (3) was added with ammonia water dropwise till pH reached 6;

(5) a mixed solution obtained by step (4) was aged for 24 h;

(6) a mixed solution after aging was centrifuged, washed with deionized water and absolute ethanol respectively, and dried in an air drying oven at 30° C. for 48 h to obtain an organic-inorganic hybrid nanoflower powder assembled by a layered rare earth compound as an inorganic carrier and the horseradish peroxidase as an organic component.

Figure 1B:
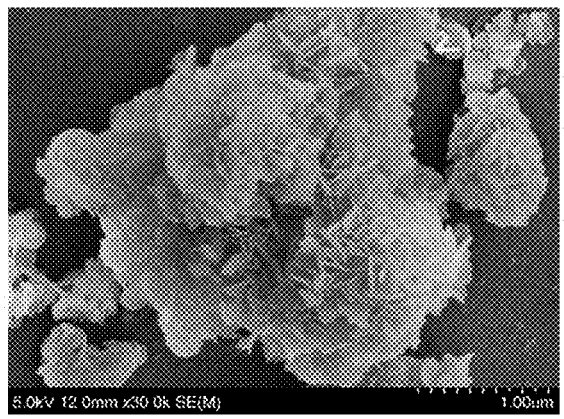

The SEM images of the organic-inorganic hybrid nanoflower prepared in this example were shown in FIGS. 1A and 1B. It can be seen from FIGS. 1A and 1B that, the organic-inorganic hybrid nanoflower assembled by the layered rare earth compound as the inorganic carrier and biological enzyme as the organic component had flower-like morphology.

Figure 2:
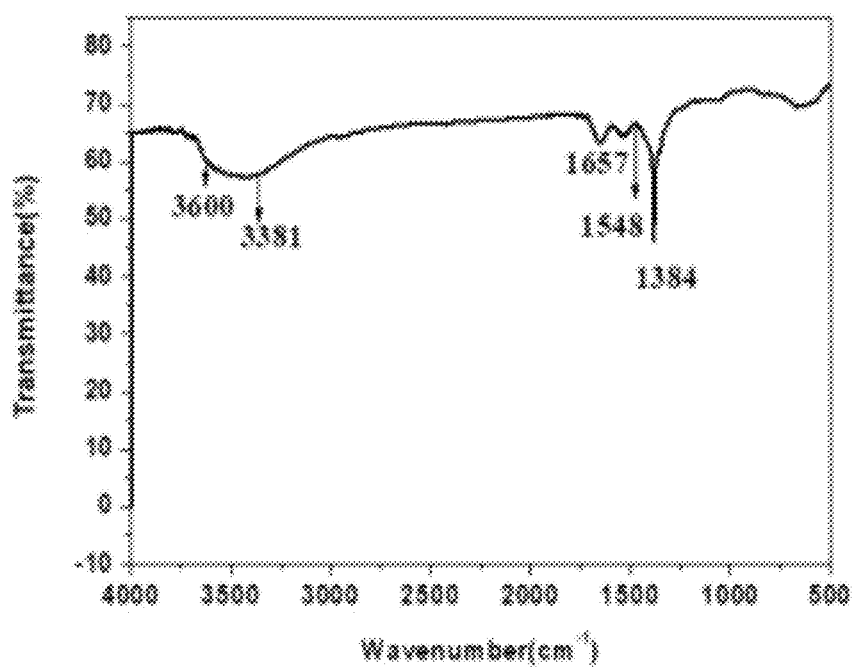
FIG. 2 is an FT-IR spectrum of the organic-inorganic hybrid nanoflower prepared in Example 1.

The FT-IR spectrum of the organic-inorganic hybrid nanoflower prepared in this example were shown in FIG. 2 where the peaks at 1657 cm-1 and 1548 cm-1 were primary amide peak and secondary amide peak, demonstrating that the biological enzyme had been loaded to the inorganic carrier successfully.

Figure 3:
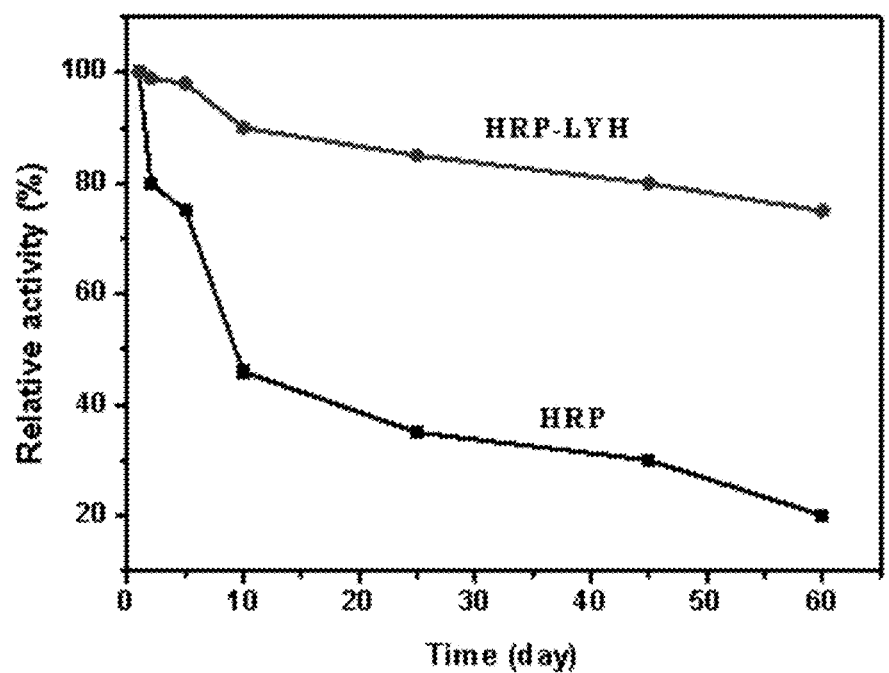
FIG. 3 shows curves comparing stabilities of the organic-inorganic hybrid nanoflower prepared in Example 1 and a free enzyme, where an upper curve represents immobilized enzyme and a lower curve represents free enzyme.
Figure 4:
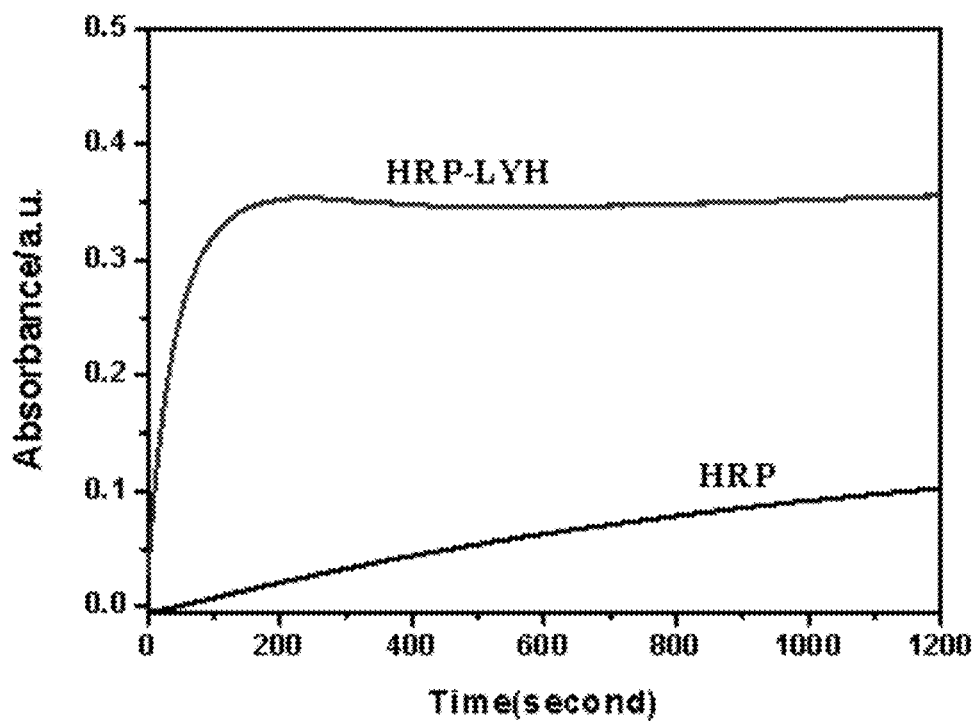
FIG. 4 shows curves comparing catalytic performances of the organic-inorganic hybrid nanoflower prepared in Example 1 and a free enzyme, where an upper curve represents immobilized enzyme and a lower curve represents free enzyme.

Stability and catalytic performance of the organic-inorganic hybrid nanoflower prepared in this example, i.e. immobilized enzyme (marked as HRP-LYH), were tested respectively using 2.5 mg/mL of free horseradish peroxidase (marked as HRP) as control. Results were shown in FIG. 3 and FIG. 4. In FIG. 3, an upper curve represented immobilized enzyme and a lower curve represented free enzyme. It can be seen from FIG. 3 that, the biological enzyme immobilized by the layered rare earth compound had better stability than the free enzyme. In FIG. 4, an upper curve represented immobilized enzyme and a lower curve represented free enzyme. It can be seen from FIG. 4 that, the biological enzyme immobilized by the layered rare earth compound had better catalytic activity than the free enzyme.

Example 2

(1) $Dy(NO_3)_3 \cdot 6H_2O$ was dissolved in deionized water to prepare a dysprosium nitrate solution with an overall concentration of rare earth ion of 0.1 mol/L;

(2) a certain amount of dysprosium nitrate solution prepared by step (1) was added with horseradish peroxidase in a concentration of 0.05 mg/mL based on the dysprosium nitrate solution at 25° C., and stirred well;

(3) a mixed solution obtained by step (2) was added with ammonium nitrate in a concentration of 0.5 mol/L based on the mixed solution and stirred well;

(4) a mixed solution obtained by step (3) was added with ammonia water dropwise till pH reached 7.6;

(5) a mixed solution obtained by step (4) was aged for 72 h;

(6) a mixed solution after aging was centrifuged, washed with deionized water and absolute ethanol respectively, and dried in an air drying oven at 45° C. for 24 h to obtain an organic-inorganic hybrid nanoflower powder assembled by a layered rare earth compound as an inorganic carrier and the horseradish peroxidase as an organic component.

The organic-inorganic hybrid nanoflower prepared in this example was similar to that in FIGS. 1A and 1B in morphology.

Figure 5:
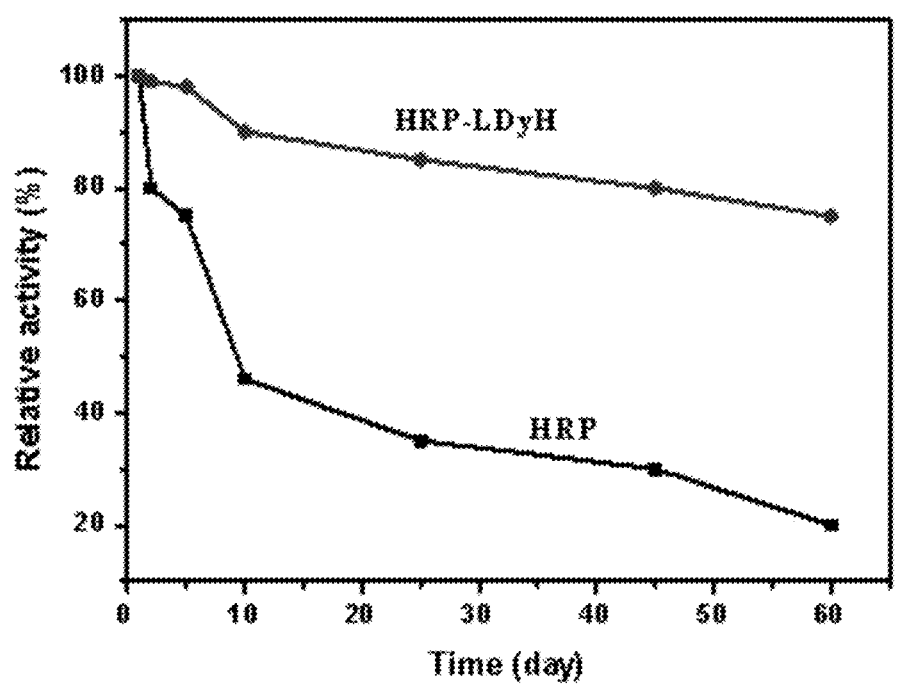
FIG. 5 shows curves comparing stabilities of the organic-inorganic hybrid nanoflower prepared in Example 2 and a free enzyme, where an upper curve represents immobilized enzyme and a lower curve represents free enzyme.
Figure 6:
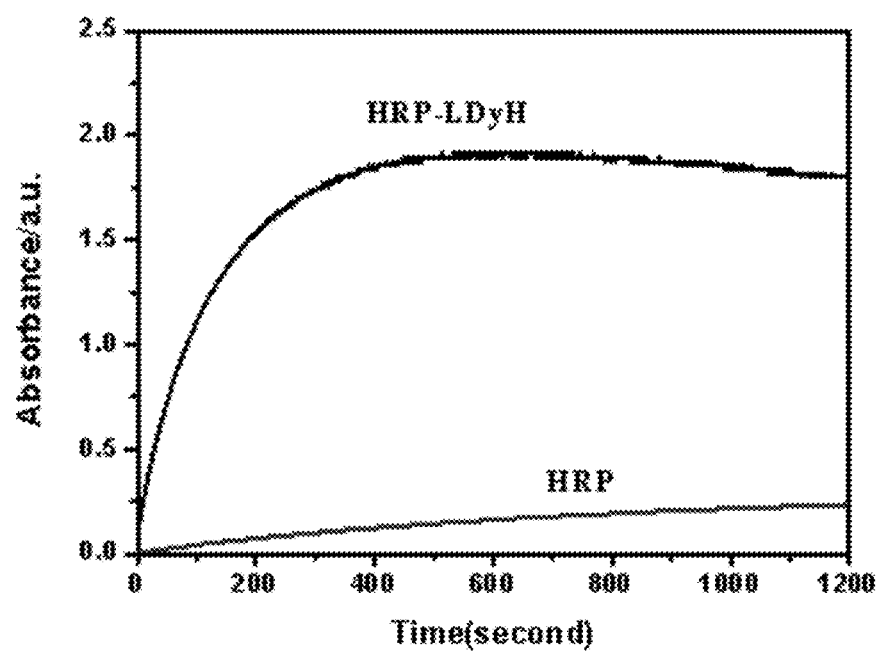
FIG. 6 shows curves comparing catalytic performances of the organic-inorganic hybrid nanoflower prepared in Example 2 and a free enzyme, where an upper curve represents immobilized enzyme and a lower curve represents free enzyme.

Stability and catalytic performance of the organic-inorganic hybrid nanoflower prepared in this example, i.e. immobilized enzyme (marked as HRP-LDyH), were tested respectively using 0.05 mg/mL of free horseradish peroxidase (marked as HRP) as control. Results were shown in FIG. 5 and FIG. 6. In FIG. 5, an upper curve represented immobilized enzyme and a lower curve represented free enzyme. It can be seen from FIG. 5 that, the biological enzyme immobilized by the layered rare earth compound had better stability than the free enzyme. In FIG. 6, an upper curve represented immobilized enzyme and a lower curve represented free enzyme. It can be seen from FIG. 6 that, the biological enzyme immobilized by the layered rare earth compound had better catalytic activity than the free enzyme.

Example 3

(1) $Y(NO_3)_3 \cdot 6H_2O$ was dissolved in deionized water to prepare a yttrium nitrate solution with an overall concentration of rare earth ion of 0.2 mol/L;

(2) a certain amount of yttrium nitrate solution prepared by step (1) was added with horseradish peroxidase in a concentration of 0.5 mg/mL based on the yttrium nitrate solution at 40° C., and stirred well;

(3) a mixed solution obtained by step (2) was added with ammonium nitrate in a concentration of 0.5 mol/L based on the mixed solution and stirred well;

(4) a mixed solution obtained by step (3) was added with ammonia water dropwise till pH reached 7;

(5) a mixed solution obtained by step (4) was aged for 72 h;

(6) a mixed solution after aging was centrifuged, washed with deionized water and absolute ethanol respectively, and dried in an air drying oven at 60° C. for 48 h to obtain an organic-inorganic hybrid nanoflower powder assembled by a layered rare earth compound as an inorganic carrier and the horseradish peroxidase as an organic component.

The organic-inorganic hybrid nanoflower prepared in this example was similar to that in FIGS. 1A and 1B in morphology.

Figure 7:
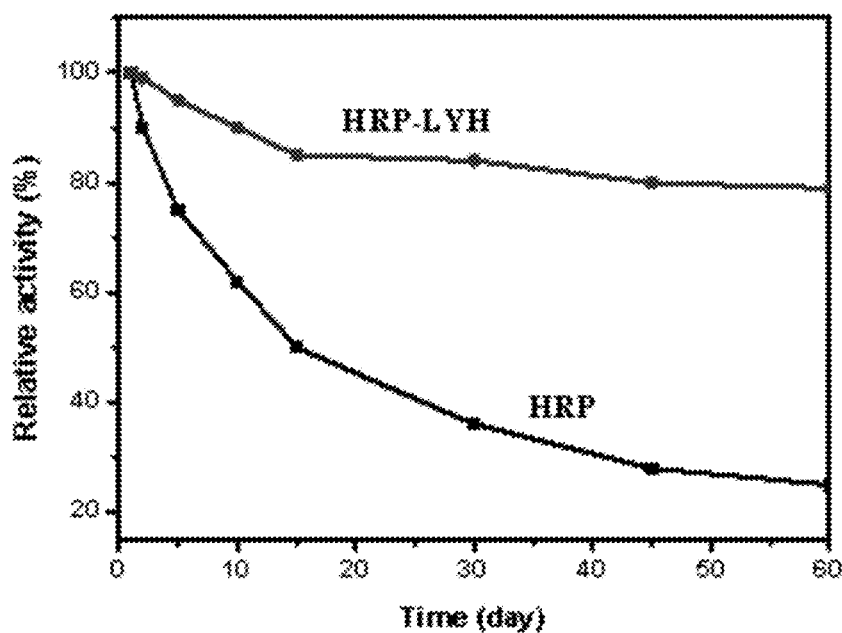
FIG. 7 shows curves comparing stabilities of the organic-inorganic hybrid nanoflower prepared in Example 3 and a free enzyme, where an upper curve represents immobilized enzyme and a lower curve represents free enzyme.
Figure 8:
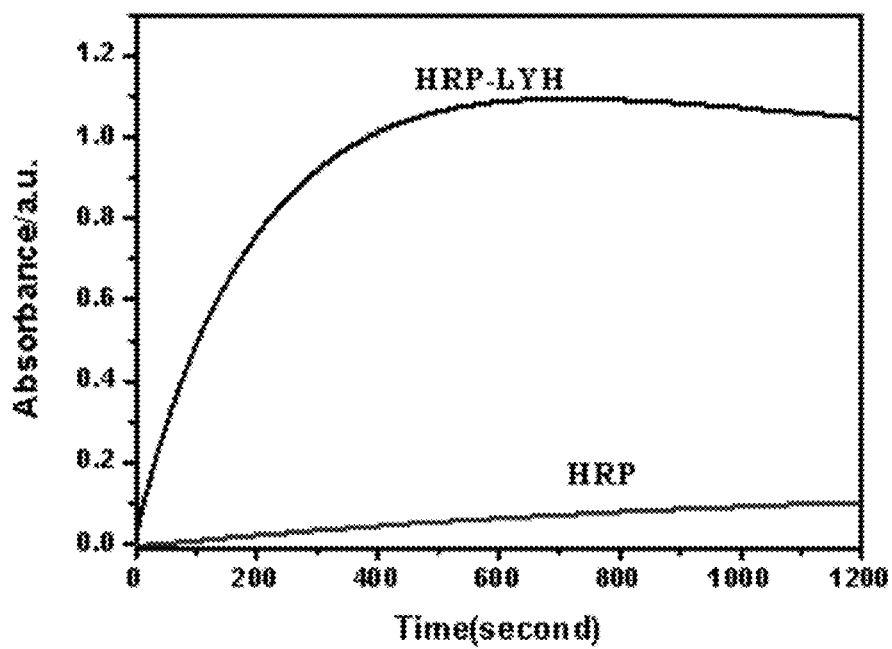
FIG. 8 shows curves comparing catalytic performances of the organic-inorganic hybrid nanoflower prepared in Example 3 and a free enzyme, where an upper curve represents immobilized enzyme and a lower curve represents free enzyme.

Stability and catalytic performance of the organic-inorganic hybrid nanoflower prepared in this example, i.e. immobilized enzyme (marked as HRP-LYH), were tested respectively using 0.5 mg/mL of free horseradish peroxidase (marked as HRP) as control. Results were shown in FIG. 7 and FIG. 8. In FIG. 7, an upper curve represented immobilized enzyme and a lower curve represented free enzyme. It can be seen from FIG. 7 that, the biological enzyme immobilized by the layered rare earth compound had better stability than the free enzyme. In FIG. 8, an upper curve represented immobilized enzyme and a lower curve represented free enzyme. It can be seen from FIG. 8 that, the biological enzyme immobilized by the layered rare earth compound had better catalytic activity than the free enzyme.

Example 4

(1) $Ho(NO_3)_3 \cdot 6H_2O$ was dissolved in deionized water to prepare a holmium nitrate solution with an overall concentration of rare earth ion of 1 mol/L;

(2) a certain amount of holmium nitrate solution prepared by step (1) was added with horseradish peroxidase in a concentration of 3 mg/mL based on the holmium nitrate solution at 45° C., and stirred well;

(3) a mixed solution obtained by step (2) was added with ammonium nitrate in a concentration of 2.5 mol/L based on the mixed solution and stirred well;

(4) a mixed solution obtained by step (3) was added with ammonia water dropwise till pH reached 5.8;

(5) a mixed solution obtained by step (4) was aged for 24 h;

(6) a mixed solution after aging was centrifuged, washed with deionized water and absolute ethanol respectively, and dried in an air drying oven at 60° C. for 48 h to obtain an organic-inorganic hybrid nanoflower powder assembled by a layered rare earth compound as an inorganic carrier and the horseradish peroxidase as an organic component.

The organic-inorganic hybrid nanoflower prepared in this example was similar to that in FIGS. 1A and 1B in morphology.

Figure 9:
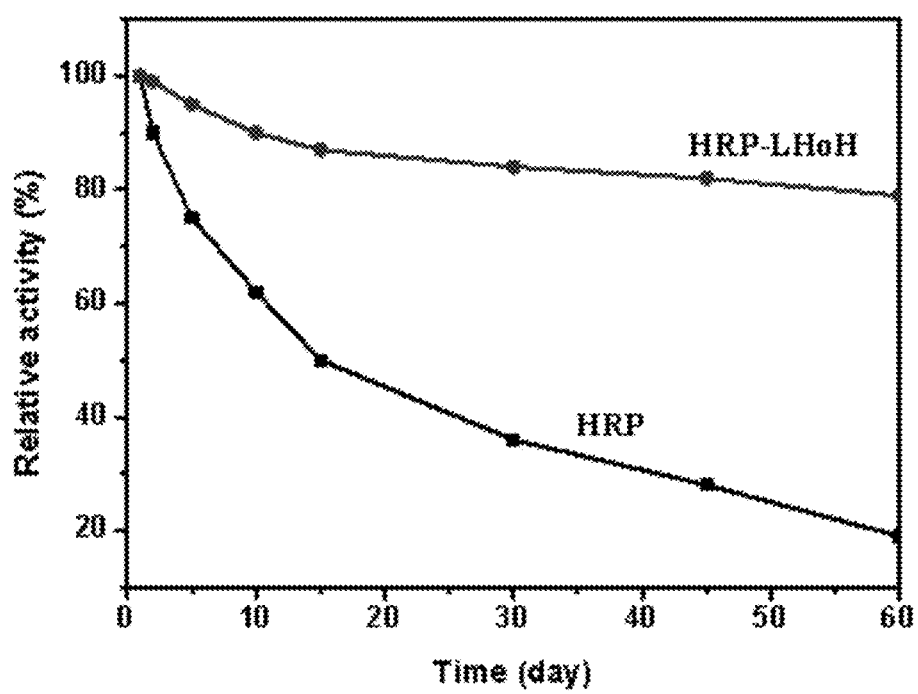
FIG. 9 shows curves comparing stabilities of the organic-inorganic hybrid nanoflower prepared in Example 4 and a free enzyme, where an upper curve represents immobilized enzyme and a lower curve represents free enzyme.
Figure 10:
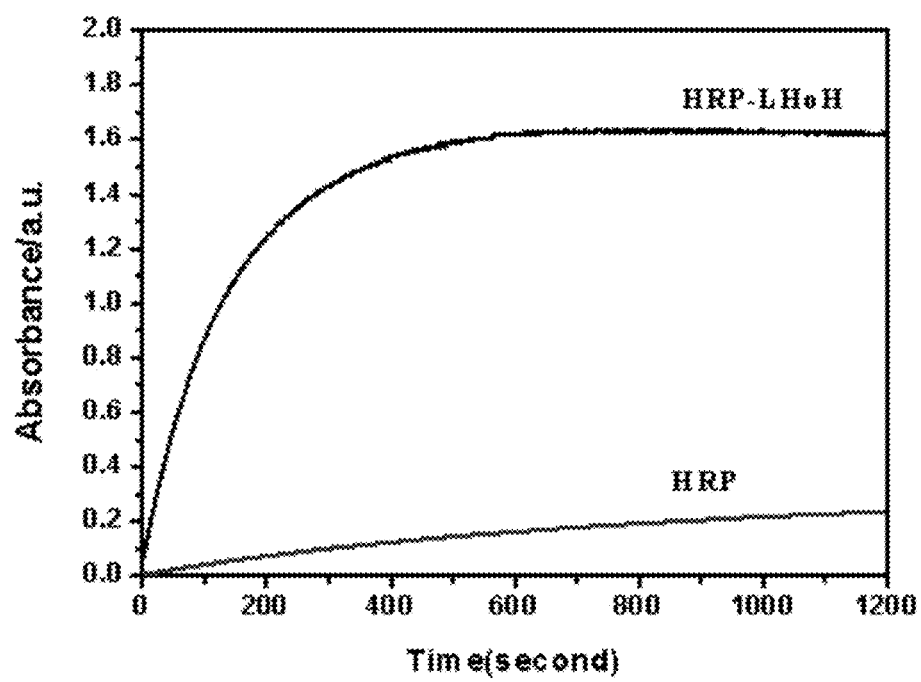
FIG. 10 shows curves comparing catalytic performances of the organic-inorganic hybrid nanoflower prepared in Example 4 and a free enzyme, where an upper curve represents immobilized enzyme and a lower curve represents free enzyme.

Stability and catalytic performance of the organic-inorganic hybrid nanoflower prepared in this example, i.e. immobilized enzyme (marked as HRP-LHoH), were tested respectively using 3 mg/mL of free horseradish peroxidase (marked as HRP) as control. Results were shown in FIG. 9 and FIG. 10. In FIG. 9, an upper curve represented immobilized enzyme and a lower curve represented free enzyme. It can be seen from FIG. 9 that, the biological enzyme immobilized by the layered rare earth compound had better stability than the free enzyme. In FIG. 10, an upper curve represented immobilized enzyme and a lower curve represented free enzyme. It can be seen from FIG. 10 that, the biological enzyme immobilized by the layered rare earth compound had better catalytic activity than the free enzyme.

Example 5

(1) $Y(NO_3)_3 \cdot 6H_2O$ was dissolved in deionized water to prepare a yttrium nitrate solution with an overall concentration of rare earth ion of 0.5 mol/L;

(2) a certain amount of yttrium nitrate solution prepared by step (1) was added with α-amylase in a concentration of 2 mg/mL based on the yttrium nitrate solution at 40° C., and stirred well;

(3) a mixed solution obtained by step (2) was added with ammonium nitrate in a concentration of 0.5 mol/L based on the mixed solution and stirred well;

(4) a mixed solution obtained by step (3) was added with ammonia water dropwise till pH reached 5;

(5) a mixed solution obtained by step (4) was aged for 72 h;

(6) a mixed solution after aging was centrifuged, washed with deionized water and absolute ethanol respectively, and dried in an air drying oven at 60° C. for 48 h to obtain an organic-inorganic hybrid nanoflower powder assembled by a layered rare earth compound as an inorganic carrier and the α-amylase as an organic component.

The organic-inorganic hybrid nanoflower prepared in this example was similar to that in FIGS. 1A and 1B in morphology.

Figure 11:
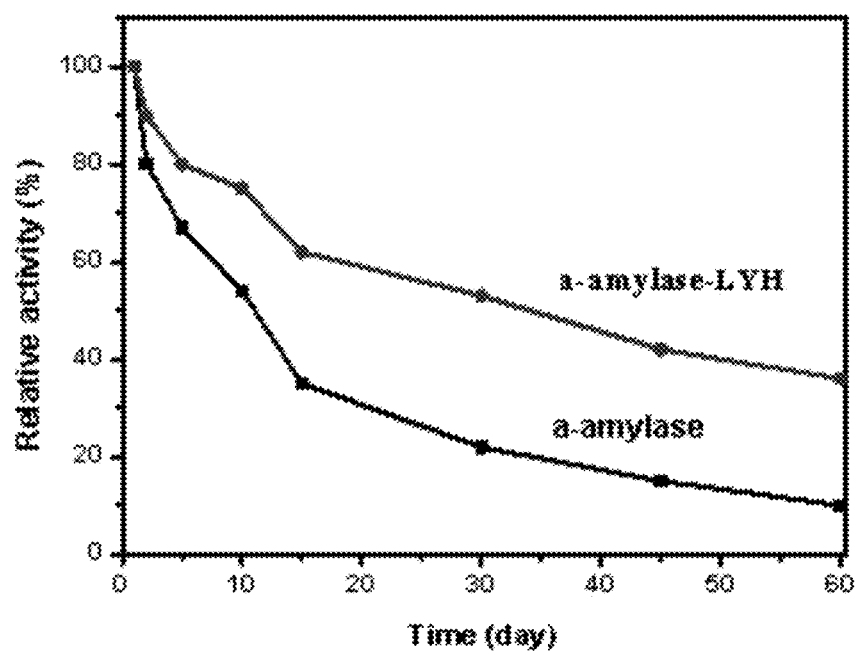
FIG. 11 shows curves comparing stabilities of the organic-inorganic hybrid nanoflower prepared in Example 5 and a free enzyme, where an upper curve represents immobilized enzyme and a lower curve represents free enzyme.
Figure 12:
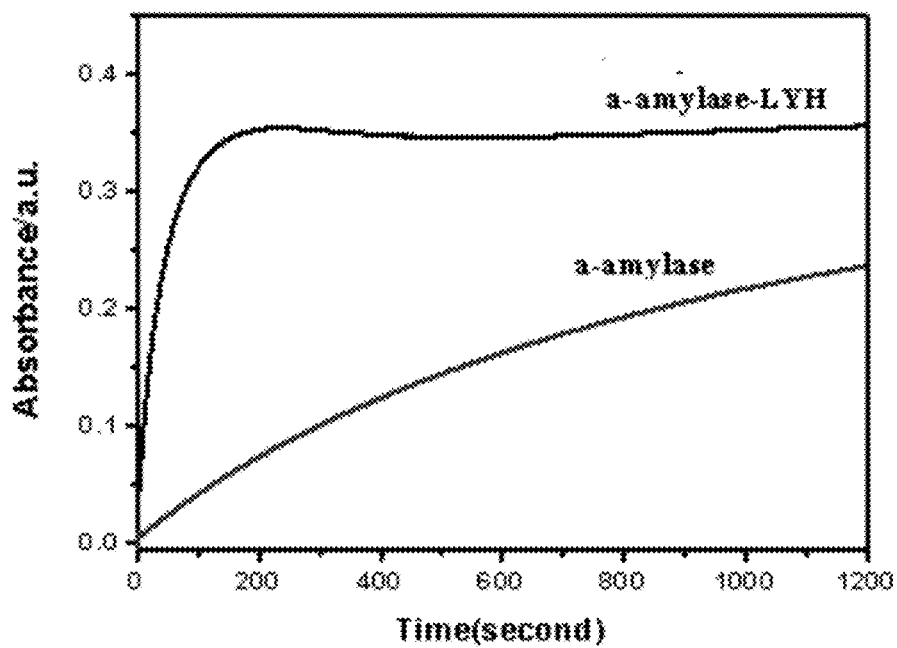
FIG. 12 shows curves comparing catalytic performances of the organic-inorganic hybrid nanoflower prepared in Example 5 and a free enzyme, where an upper curve represents immobilized enzyme and a lower curve represents free enzyme.

Stability and catalytic performance of the organic-inorganic hybrid nanoflower prepared in this example, i.e. immobilized enzyme (marked as a-amylase-LYH), were tested respectively using 2 mg/mL of free α-amylase (marked as a-amylase) as control. Results were shown in FIG. 11 and FIG. 12. In FIG. 11, an upper curve represented immobilized enzyme and a lower curve represented free enzyme. It can be seen from FIG. 11 that, the biological enzyme immobilized by the layered rare earth compound had better stability than the free enzyme. In FIG. 12, an upper curve represented immobilized enzyme and a lower curve represented free enzyme. It can be seen from FIG. 12 that, the biological enzyme immobilized by the layered rare earth compound had better catalytic activity than the free enzyme.

Example 6

(1) Y(NO3)3·6H2O was dissolved in deionized water to prepare a yttrium nitrate solution with an overall concentration of rare earth ion of 0.3 mol/L;

(2) a certain amount of yttrium nitrate solution prepared by step (1) was added with laccase in a concentration of 2 mg/mL based on the yttrium nitrate solution at 40° C., and stirred well;

(3) a mixed solution obtained by step (2) was added with ammonium nitrate in a concentration of 1 mol/L based on the mixed solution and stirred well;

(4) a mixed solution obtained by step (3) was added with ammonia water dropwise till pH reached 8;

(5) a mixed solution obtained by step (4) was aged for 72 h;

(6) a mixed solution after aging was centrifuged, washed with deionized water and absolute ethanol respectively, and dried in an air drying oven at 45° C. for 48 h to obtain an organic-inorganic hybrid nanoflower powder assembled by a layered rare earth compound as an inorganic carrier and the laccase as an organic component.

The organic-inorganic hybrid nanoflower prepared in this example was similar to that in FIGS. 1A and 1B in morphology.

Figure 13:
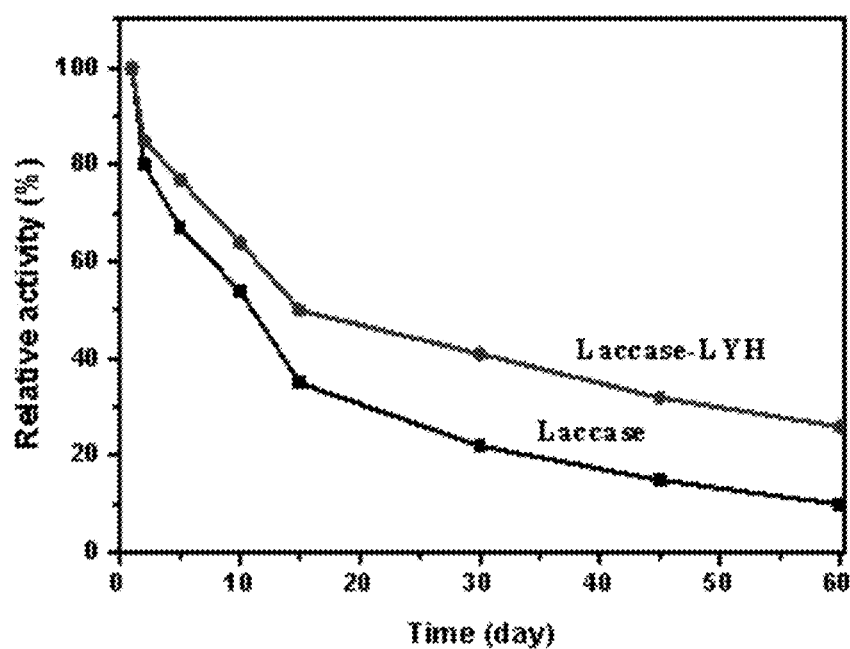
FIG. 13 shows curves comparing stabilities of the organic-inorganic hybrid nanoflower prepared in Example 6 and a free enzyme, where an upper curve represents immobilized enzyme and a lower curve represents free enzyme.
Figure 14:
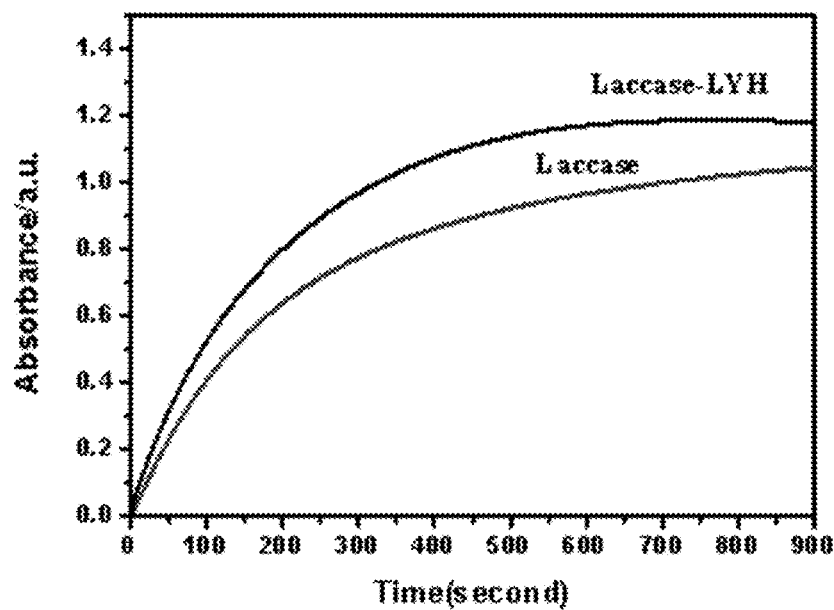
FIG. 14 shows curves comparing catalytic performances of the organic-inorganic hybrid nanoflower prepared in Example 6 and a free enzyme, where an upper curve represents immobilized enzyme and a lower curve represents free enzyme.

Stability and catalytic performance of the organic-inorganic hybrid nanoflower prepared in this example, i.e. immobilized enzyme (marked as Laccase-LYH), were tested respectively using 2 mg/mL of free laccase (marked as Laccase) as control. Results were shown in FIG. 13 and FIG. 14. In FIG. 13, an upper curve represented immobilized enzyme and a lower curve represented free enzyme. It can be seen from FIG. 13 that, the biological enzyme immobilized by the layered rare earth compound had better stability than the free enzyme. In FIG. 14, an upper curve represented immobilized enzyme and a lower curve represented free enzyme. It can be seen from FIG. 14 that, the biological enzyme immobilized by the layered rare earth compound had better catalytic activity than the free enzyme.

It can be seen from the above examples that, the flower-like immobilized enzymes of the present invention formed by layered rare earth compounds as inorganic carriers for biological enzymes had desirable stability and higher catalytic performance compared with free enzymes. Moreover, the preparation method provided by the present invention adopted mild conditions in a simple process which took a relatively short time.

The above descriptions are merely preferred implementations of the present invention. It should be noted that a person of ordinary skill in the art may further make several improvements and modifications without departing from the principle of the present invention, but such improvements and modifications should be deemed as falling within the protection scope of the present invention.

What is claimed is:
1. An organic-inorganic hybrid nanoflower, comprising:
a flower-like immobilized enzyme formed by self-assembly of a layered rare earth compound as an inorganic carrier, wherein the layered rare earth compound is $Ln_2(OH)_5NO_3 \cdot nH_2O$, wherein Ln is one or more of La, Ce, Pr, Nd, Sm, Eu, Gd, Tb, Dy, Ho, Er, Tm, Yb or Y, and n=1.1-2.5; and
a biological enzyme as an organic component, wherein the biological enzyme is one or more of α-amylase, horseradish peroxidase, or laccase.

* * * * *